US006127188A

United States Patent [19]
Sullivan

[11] Patent Number: 6,127,188
[45] Date of Patent: Oct. 3, 2000

[54] METHOD AND APPARATUS FOR CONTROLLING EVAPORATION IN HISTOLOGICAL PROCEDURES

[75] Inventor: Daniel E. Sullivan, Cambridge, Mass.

[73] Assignee: MJ Research, Inc., Watertown, Mass.

[21] Appl. No.: 09/468,145

[22] Filed: Dec. 21, 1999

Related U.S. Application Data

[63] Continuation of application No. 08/540,090, Oct. 6, 1995.

[51] Int. Cl.$^7$ .................................................. G01N 33/00
[52] U.S. Cl. .............................. 436/94; 435/6; 435/91.1; 435/91.2; 435/194; 424/78.24
[58] Field of Search .............................. 435/6, 91.1, 91.2, 435/183, 194, 287.2; 436/94; 536/23.1, 24.3, 24.33; 424/78.24

[56] References Cited

U.S. PATENT DOCUMENTS

| | | |
|---|---|---|
| 5,326,692 | 7/1994 | Brinkley et al. .............................. 435/6 |
| 5,346,672 | 9/1994 | Stapleton et al. . | 
| 5,382,511 | 1/1995 | Stapleton . |
| 5,492,837 | 2/1996 | Naser-Kolahzadeh et al. ......... 436/176 |
| 5,541,066 | 7/1996 | Sandell ........................................ 435/6 |

OTHER PUBLICATIONS

"In situ Hybridization to cellular RNA", Current Protocols. John Wiley & Sons (1989), Sections 14.3.1–14.3.14.
"Immunohistochemistry", Current Protocols, John Wiley & Sons (1989) Sections 14.6.1–14.6.13.
"In situ Hybridization and detection using nonisotopic probes" Unit 14.3, Sections Sections 14.7.1–14.7.14.
"In situ Polymerase chain reaction and hybridization to detect low–abundance nucleic acid targets". Current Protocols, John Wiley & Sons (1995), Sections 14.8.1–14.8.24.
Staecker, Hinrich et al., (1994) A procedure for RT–PCR amplification of mRNAs on histological specimens. "Bio-Techiques", vol. 16, No. 1, pp76–80.
Sooknanan, Roy and Malek, Lawrence T. NASBA: A detection and amplification system uniquely suite for RNA, "Bio/Technology", vol. 13, Jun. 1995, pp 563–564.

Zehbe, Ingeborg et al., (1994) Self–sustained sequence replication–based amplification (3SR) for the in situ detection of mRNA in cultured cells. "CellVision", vol. 1, No. 1, pp20–24.
Gosden, J. et al., (1991) Oligonucleotide–primed in situ DNA synthesis (PRINS): A method for chromosome mapping, banding, and investigation of sequence organization. Cytogen,CellGenet57:100–4.
"Current Protocols in Molecular Biology", F.M. Ausubel et al., eds., John Wiley & Sons, Inc., Sections 14.3 & 14.7.
"Current Protocols in Molecular Biology", F.M. Asubuel et al., eds., John Wiley & Sons, Inc., Section 14.8.
Steacker, H., Cammer, M., Rubenstein, R., & Van de Water, T.R., 1994, A procedure for RT–PCR amplification of mRNAs on histological specimens, "BioTechniques", 16:76–80.
Sookannan, R., and Malek, L.T., 1995, NASBA. A detection and amplification system uniquely suited for RNA, "Bio/Technology", 13:563–564.
Zehba, I., Hacker, G.W., Sallstrom, J.F., Rylander, E., & Wilander, E. 1994, Self–sustained sequence replication–based amplification (3SF) for in–situ detection of mRNA in culture cells, "Cell Vision" 1:20–24.
Gosden, J., Hanratty, D., Starling, J., Fantes, J., Mitchell, A., & Porteous, D. 1991, Oligonucleotide–primed in situ DNA synthesis (PRINS): a method for chromosome mapping, banding and investigation of sequence organization. "Cytogenet. Cell Genet," 57:100–104.
Watkins, S. 1989, Immunohistochemistry, in: "Current Protocols in Molecular Biology", F.M. Ausubel et al., eds., John Wiley & Sons, Inc., Section 14.6.

*Primary Examiner*—Bradley L. Sisson
*Attorney, Agent, or Firm*—Mintz, Levin, Cohn, Ferris, Glovsky and Popeo, P.C.

[57] ABSTRACT

A method and apparatus is disclosed to reduce evaporation of solutions, particularly aqueous solutions, using a polymeric material such as polysucrose, polyvinylpyrrolidone and polyethylene glycol. A microscope slide and cover glass assembly utilizing the polymeric material in solution and method of use are described.

6 Claims, 6 Drawing Sheets

METHOD AND APPARATUS FOR CONTROLLING EVAPORATION IN HISTOLOGICAL PROCEDURES

This application is a continuation application under 37 CFR §1.53(b)(1) of Ser. No. 08/540,090, filed Oct. 6, 1995, incorporated herein by reference.

FIELD OF INVENTION

This invention relates to an improved method and apparatus, and in particular, additives which reduce the rate of evaporation of solutions during ambient or above ambient temperature procedures. The invention has particular application in the preparation and preservation of fluids encapsulated between a microscope slide and a cover glass in temperature cycling operations.

BACKGROUND IN THE INVENTION

The study of physical and functional characteristics of biological tissues (histology) often involves affixing cells or thin tissue sections to a support such as a glass microscope slide. The affixed tissue materials are then subjected to various procedures such as differential staining to reveal specific features of the tissue upon subsequent microscopic examination.

Many of these procedures, such as staining, can be done by immersing the slide in a large excess of the test solution containing the stain. Total slide immersion is not feasible for some procedures due to the attributes of either the test solution (e.g., cost, scarcity, safety) and/or the procedure (e.g., the need for rapid temperature changes). In such cases, it is desirable to use a minimal volume (e.g., less than 0.1 ml) of the test solution in direct contact with the tissue being investigated. Such minimal volume procedures include: nucleic ambient temperatures. The test solution also may be rapidly cycled among a variety of temperatures ranging up to nearly 100° C. Because the concentration of components in the test solution is critical to success of the procedure, there is an obvious need to control evaporation of the water from the minimal volume test solution on the microscope slide during the procedures.

Various methods have been devised to control evaporation from microscope slides. For some procedures where the temperature is held constant (e.g., nucleic acid hybridizations), the slide with a drop of the test solution over the tissue material can simply be placed in a humidified chamber at the appropriate temperature. This works adequately well but requires a temperature controlled instrument with an appropriate humidification source. If the procedure requires a changing temperature regime, however, humidified chambers are not appropriate due to problems associated with condensation and evaporation occurring during thermal transitions.

An obvious method of eliminating evaporation is to create a small chamber directly on the microscope slide over the tissue material. The chamber contains the test solution, excludes air and is sealed by some mechanism so that evaporation is minimized or eliminated. Traditionally, chambers have been made by positioning a standard cover glass over the tissue material with a layer of the test solution contained between the cover glass and the slide. Microscope slides in common use may have printed surface patterns which define separate areas of the slide and provide a raised frame to hold the cover glass a fixed distance above the surface of the slide. To seal the chamber, some practitioners immerse the slide with the test solution over the tissue and a cover glass in place in a small volume of a non-water miscible fluids, e.g., mineral oil. This method has a number of disadvantages. It does not guarantee that the aqueous test solution will stay over the tissue material. It is difficult to perform rapid thermal cycling. Furthermore, it is very messy and requires extensive rinsing with non-aqueous solvents to remove the mineral oil after the procedure is completed.

To create a sealed chamber without the use of mineral oil in prior art practices, the edges of the cover glass have been sealed to the slide by a variety of means well known in the art including fingernail polish, rubber cement and various commercially available glues. These sealing methods are tedious, messy, can involve the inhalation by the user of organic solvents, are prone to failure, or worse, they can "poison" the test reactions if not applied correctly. In addition, fingernail polish is the only one of these sealing methods suitable for the higher temperature thermal cycling procedures. Another problem with these sealants is experienced when removing them and the cover glasses after the procedure is ended. Removal requires soaking in solvents (e.g., ethanol or xylene) and/or careful manipulation with a razor blade followed by scraping to remove residual sealant from the slide.

Various commercially available chambers for affixing to microscope slides have been marketed as alternatives to the above mentioned sealants. These commercially available chambers use: a) simple adhesion of a smooth rubber gasket to the glass slide to affix the chamber (such as a product called Probe Clips™, available from Grace BioLabs); b) a pressure sensitive adhesive around the periphery of a molded plastic funnel shaped device (including a product called Gene Wells™, available from Techne, Inc., Princeton, N.J.; and a product called Gene Cone™, available from Gene Tec Corp., Durham, N.C.); or c) small silicone chambers "sealed" by pressure to the slide using a stainless steel clip mechanism (a product called Amplicover™ Discs and Clips, available from the Applied Biosystems Division of Perkin Elmer Corp., Foster City, Calif.), described in U.S. Pat. No. 5,364,790 issued Nov. 15, 1994 and assigned to the Perkin-Elmer Corporation. The Probe Clips™ product has been found to provide insufficient adhesion to maintain a seal at elevated temperatures especially on slides which are not extremely clean and therefore cannot be used for most thermal cycling procedures. The Gene Cones™ product has been found to require a heat step of 95° C. for 15 seconds to fix the adhesive before a test solution can be added. This heat step is not only inconvenient but may be incompatible with some tissue materials. In addition, each Gene Cone™ product covers a limited area of the slide and the cone extends several millimeters above the slide surface, rendering this product incompatible with a number of commercially available slide thermal cycling instrumentation. The Amplicover™ Disks and Clips products are part of an integrated system requiring the use of special thick slides (thus limiting their utility for archival histological preparations), special disposables and a costly assembly tool as well as a specifically designed thermal heating block. In addition, the Amplicover™ Disk products provide only a limited area of tissue material coverage.

Another commercially available device sandwiches the microscope slide between larger rigid plates and has a silicone pad over the slide with holes in the pad corresponding to the areas where the tissue is affixed. Holes with removable plugs in the top plate allow test solutions to be added to the chambers formed by the pad. This product is called the Thermo-Slide™ Block, available from Elmeco Engineering, Rockville, Md. The Thermo-Slide™ Block product is designed to passively rest on the surface of a separate thermal plate or thermal cycler. The Thermo-Slide™ Block product has a number of limitations. It holds only two slides and has a thermal mass sufficient to render thermal cycling quite slow and, therefore, provide poorly defined thermal profiles on the slides.

A factor common to the above methods is the requirement of the user to manipulate each slide in one or more operations in order to control evaporation. Any method and apparatus which eliminates user handling of the slides would be beneficial not only for a particular procedure but also in the future development of automated slide handling systems.

In summary, therefore, the current methods and apparatus used to control evaporation during minimal volume histological procedures on microscope slides suffer from a variety of deficiencies. These include: a) limited thermal range; b) inability to use for thermal cycling procedures; c) tedious application; d) messy to use and clean-up afterwards; e) possible adverse affects on the test procedure; f) a requirement for special microscope slides; g) limited tissue material coverage; h) a requirement for expensive equipment and/or disposables; and, I) resistance to automated handling. Therefore, what is desired in method and apparatus to control evaporation which eliminates or substantially reduces many of the above deficiencies, and yet remains a cost-effective alterative to the prior art methods and apparatus discussed above.

SUMMARY OF THE INVENTION

Accordingly, it is among the several objects and advantages of the present invention to provide a method of controlling evaporation which operates up to at least 97° C.; to provide a method of controlling evaporation even in thermal cycling applications; to provide a method of controlling evaporation which eliminates the application of exogenous sealing materials (e.g., fingernail polish or glue); to provide a method of controlling evaporation which is easy to use and easy to remove from the slides after use; to provide a method of controlling evaporation which will not adversely affect the test procedure; to provide a method of controlling evaporation which can be used with standard microscope slides; to provide a method of controlling evaporation which can cover the full functional area of the microscope slide; to provide a method of controlling evaporation which does not require extra equipment or disposables; and, to provide a method of controlling evaporation which is amenable to automated handling.

In order to achieve the above referenced objects and advantages, the present invention incorporates the use of non-ionic organic polymers such as polymers of sucrose (polysucrose), which are mixed in a mixed in aqueous solution and placed over the tissue sample. A cover glass is then placed over the aqueous solution containing the polymer. It can be seen that with the cover glass in place, the only surfaces from which evaporation can occur are at the edge portions where the cover glass and the glass slide meet. As water evaporates from the aqueous solution, the polymers contained in the solution form a boundary at the interface between the solution and the external environment, thus minimizing further evaporation.

Further objects and advantages are to provide a method of controlling evaporation which is functional in a wide variety of enzymatic and biochemical reactions. Still further objects and advantages will become apparent from a consideration of the following detailed description and drawings.

DETAILED DESCRIPTION OF THE INVENTION

The present invention is directed to an apparatus, a formulation or composition of matter and a method for its use in which one or more polymeric components are added to existing test solutions in order to effect a significant reduction of evaporation from the test solution, particularly during thermal cycling. The chemical constituents of the present invention are generally non-ionic organic polymers of molecular weight generally (but not necessarily) greater than 1000. As water evaporates from the test solution, it has been found that the polymers form a boundary at the interface between the test solution and the external environment, that is, at the exposed surface of the test solution between the cover glass and the microscope slide. This boundary becomes progressively less permeable to water as thermal cycling continues, thereby reducing the evaporation of water from the test solution. The present invention, therefore, eliminates the need for exogenously added sealants or mechanical pressure devices of the prior art described above to reduce evaporation from test solutions.

The polymers used in this invention are typically polymers of sucrose having average molecular weights of 70,000 and 400,000, commonly referred to as polysucrose or commercially available Ficoll™, available from Pharmacia, Inc., Uppsala, Sweden. Other polymers which can be used in this invention include poly[1-(2-oxo-1-pyrrolidinyl)ethylene], commonly referred to as polyvinyl pyrrolidone, and various polymeric lengths of polyethylene glycol and its derivatives. The polymers are used at final concentrations up to 50% (w/w) in the test solutions, typically 15% in the case of the preferred polymer, polysucrose (average molecular weight= 70,000). For convenience, the polymers with or without some other test solution components can be prepared as a concentrate, e.g., a 2× concentrate [=30% polysucrose], allowing the user to prepare the final 1× test solution by the addition of water and other test components. Preparing the polymers as a concentrate and thus allowing the user to "custom blend" the final solution also gives the invention the versatility to be used with a variety of test procedures. While the polymeric materials are known, to the best of the inventor's knowledge, they have never been put to the use and in the assembly and method disclosed and claimed in the present application.

The present invention is effectively used with a typical microscope slide and cover glass assembly as shown in FIG.

Figure 1A:
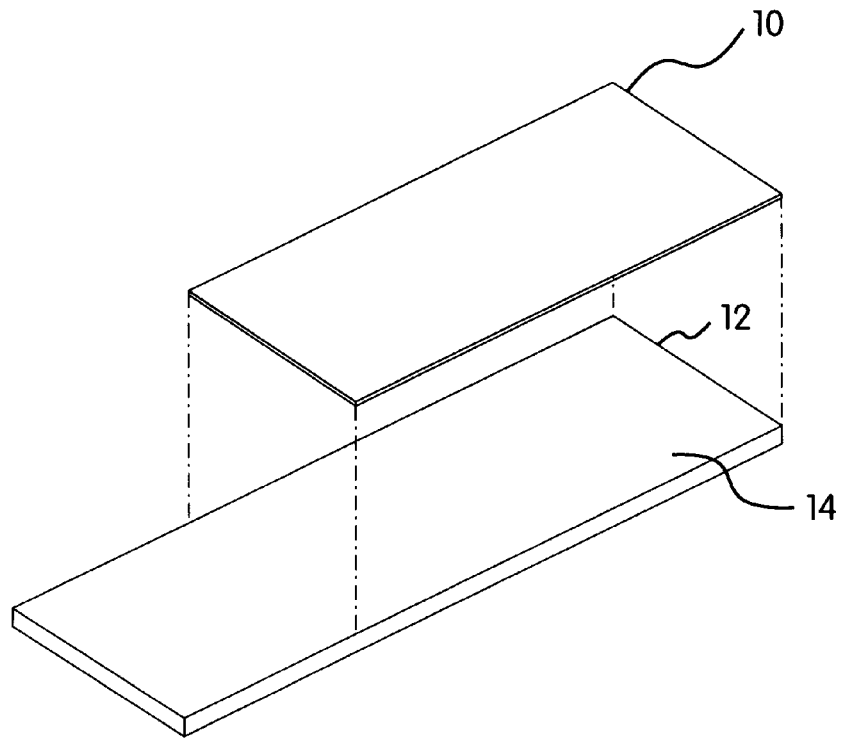
FIGS. 1A and 1B illustrate a typical microscope slide and cover glass assembly in the disassembled and assembled configurations respectively.

1. Referring now to FIG. 1A, there is illustrated a microscope slide 12 of typical dimensions 2.5 centimeters (cm) by 7.5 cm by 1 millimeter (mm) thick, which provides a surface 14 on which the biological tissue material is affixed. The test solution is applied to the surface 14. Then, a cover glass 10 is placed on the test solution creating the assembly shown in FIG. 1B. The cover glass may be round (16–25 mm diameter), square or rectangular of a variety of dimensions from 16×16 mm to 25×60 mm, and can be of a variety of thicknesses, but is typically between 0.13–1 mm in thickness.

Figure 1B:
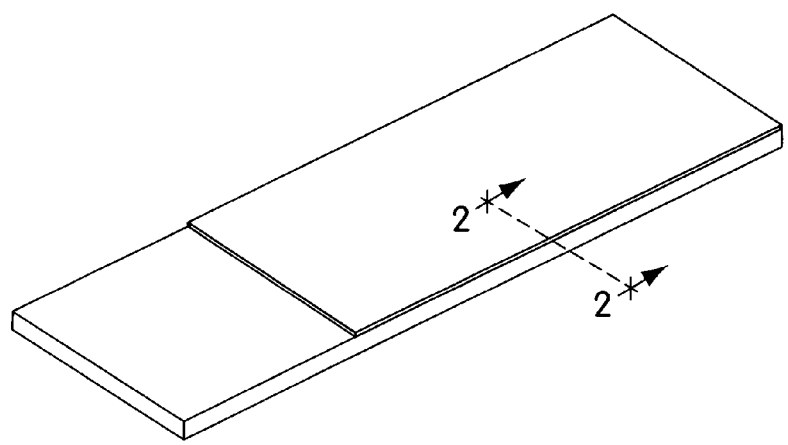
Figure 2A:
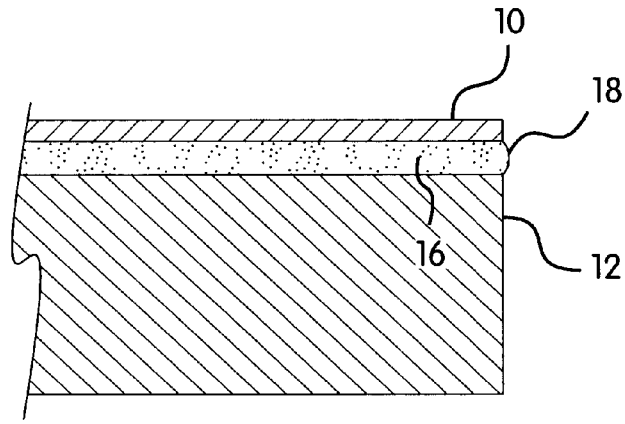
FIGS. 2A–2C provide enlarged sectional views illustrating a sequence of modes of operation of the present invention.
Figure 2B:
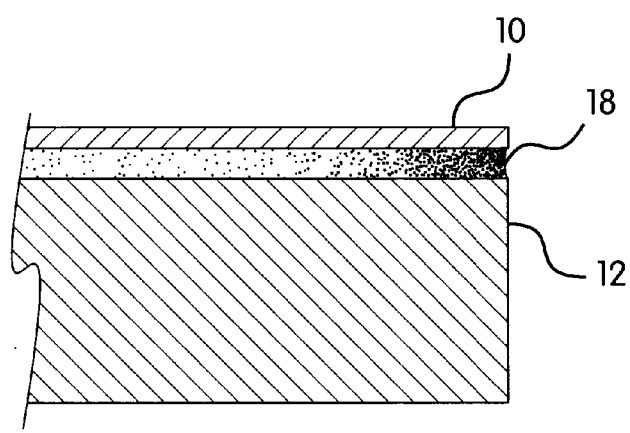
Figure 2C:
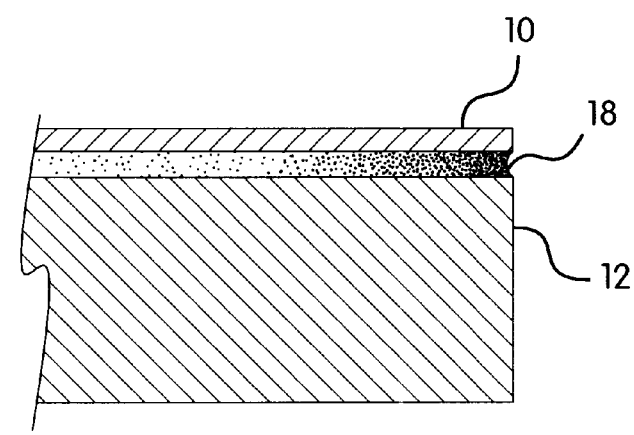

The view along line 2—2 in FIG. 1B is illustrated in FIGS. 2A–2C. These figures illustrate a sequence in the operation of the present invention and are enlarged to better illustrate the sequence of operation. Referring to FIG. 2A, when the cover glass 10 is first placed on the test solution 16, the cover glass is seen to float on, and be supported by, the test solution. The cover glass may, however, be supported by structural features (not shown, but well-known in the art) projecting upward from the slide surface 14 or features projecting downward from the lower surface of the cover glass 10, without adversely affecting the performance of the present invention. The surface of the test solution exposed to the atmosphere defines an interface 18 from which water can evaporate from the test solution to the atmosphere. As water evaporates from the interface 18, the polymeric components of the present invention, being non-volatile, are left behind in the aqueous side of the total solution/atmosphere interface where it has found they progressively concentrate and reduce the rate of evaporation. This progressive concentration of components is illustrated by the density of the dots in the test solutions at the interfaces in FIGS. 2A, 2B and 2C. As the volume of the test solution decreases due to the initial evaporation, the cover glass may move progressively closer to the microscope slide. The concentrated components of the present invention not only act to reduce evaporation but can also act to support the cover glass (if it is not already supported by some other structural features described above) thus defining the chamber containing the test solution.

Many practitioners use microscope slides which have a printed pattern on the upper surface 14. Such raised patterns define between them an area(s) used for the tissue materials. As well, the pattern can also act as a support for the cover glass. Such printed patterns are typically 0.0125 to 0.025 mm in height, and will define a minimal volume of the chamber containing the test solution when the cover glass is supported by the printed pattern. In practice, it is very difficult to use only the volume of test solution which would fill the chamber defined by the printed pattern (typically less than 20 microliters [$\mu l$]) without trapping air bubbles over the tissue. For this reason, it is often desirable to add a larger than minimally required volume of test solution to the slide. The skill of the practitioner determines the actual volume which can be effectively applied to the slide without trapping air. Nevertheless, the present invention remains operative throughout the entire range of possible volumes which may be used.

Figure 3:
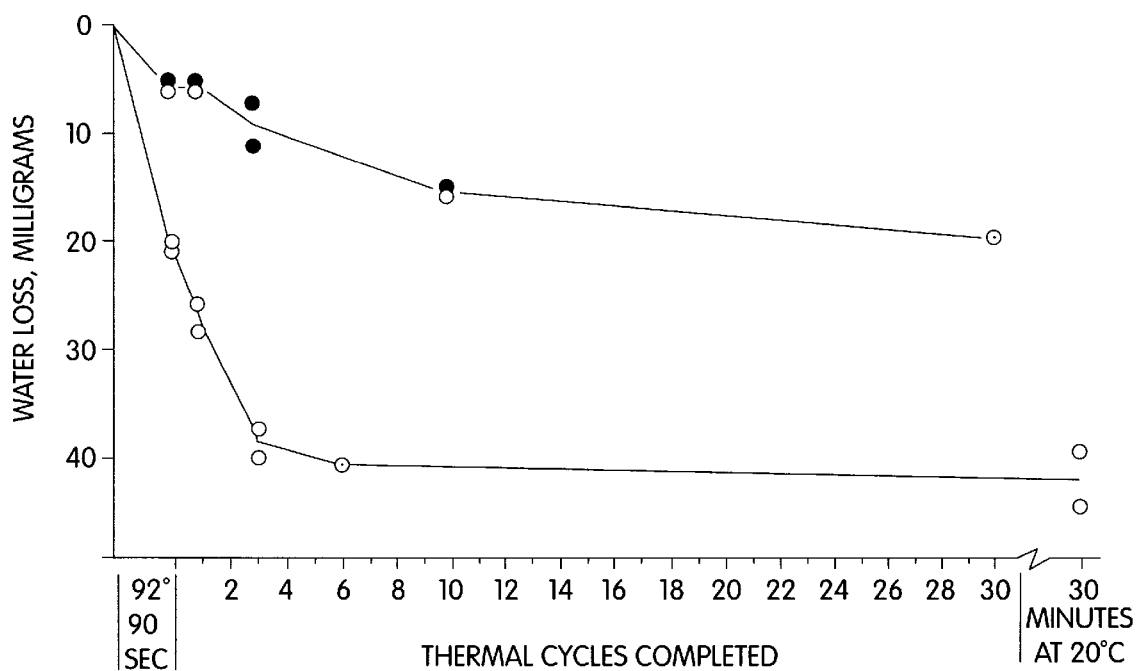
FIG. 3 graphically illustrates the beneficial effects of the present invention on water loss from microscope slides with cover glasses during a typical thermal cycling procedure.

FIG. 3 provides data extracted from examples showing the operation of the present invention in being able to reduce water loss from microscope slides cycled through a thermal cycling protocol, a common use of the present invention. The slides used in these examples had a printed pattern approximately 0.0125 mm thick on the upper surface. The pattern defined one rectangular area approximately 1.7×4.7 cm. The pattern thus defined a final minimal chamber volume of approximately 0.010 cubic centimeters (cc) which equals 10 microliters ($\mu l$). Fifty $\mu l$ of a test solution with or without 15% polysucrose were added to each microscope slide. A cover glass was positioned on each, and the assembled test slides were weighed to +/−1 mg. The assembled slides were placed in a thermally controlled block designed for microscope slides, in this case an instrument part number PTC-100-16MS, available from MJ Research, Watertown, Mass., the assignee of the present invention. The slides were subjected to the following thermal protocol: 92° C. for 90 seconds followed by 30 cycles of 94° C. for 30 seconds, then 45° C. for one minute, then 72° C. for one minute. After the 30th cycle, the slides were maintained at 20° C.

At various times during the protocol, slides were removed from the temperature controlled block, re-weighed and the water loss recorded as "milligrams loss" (1 milligram=1 microliter of water). Referring to FIG. 3, it can be seen that the slides containing test solution with 15% polysucrose (filled circles) had greatly reduced water loss compared to the slides with test solution without the polysucrose (open circles). Test solution without polysucrose had evaporated to near dryness by the sixth thermal cycle. The solutions with polysucrose remained liquid throughout the test without intrusion of air under the cover glass. The water loss of 20 milligrams (=20 $\mu l$) from the test solutions containing polysucrose is explainable by recalling the discussion of FIG. 2. The cover glass is initially floating on a volume of test solution in excess of what would be minimally required to fill the chamber defined by the printed pattern (in the case of FIG. 3, 10 $\mu l$). Water evaporates from the interface until the concentrated components around the periphery support the cover glass with a minimally permeable water barrier. Referring to FIG. 3, it is seen at this point was reached by approximately the tenth cycle (15 $\mu l$ loss). Subsequently, only 5 $\mu l$ was lost in the next 20 cycles. Without the presence of components of the present invention, water rapidly evaporates to dryness, the printed pattern not acting as an effective barrier to evaporation. With the inclusion of the polymeric components in the aqueous solution of the present invention, it has been found that the cover glass becomes supported well above the printed ink pattern, retaining a test solution volume much greater than would be defined by the printed pattern alone.

Another issue of concern to practitioners is the possible excessive concentration of reactants in the liquid as water evaporates. This is addressed in the example illustrated in FIGS. 4A and 4B. A slide and cover glass assembly with 50 $\mu l$ of a test solution containing 15% polysucrose and a visible blue dye was thermally cycled and periodically weighed as described in FIG. 3. Prior to thermal cycling ("0") and periodically through the cycling procedure, the slide assembly was digitally imaged in order to analyze the dye density from one edge of the slide assembly to the other edge. The slide and cover glass assembly was also imaged prior to adding the dye test solution (E in FIG. 4B). The digitized images were analyzed by plotting 5 pixel wide profiles of the same section across the full width of the slide assembly.

Figure 4A:
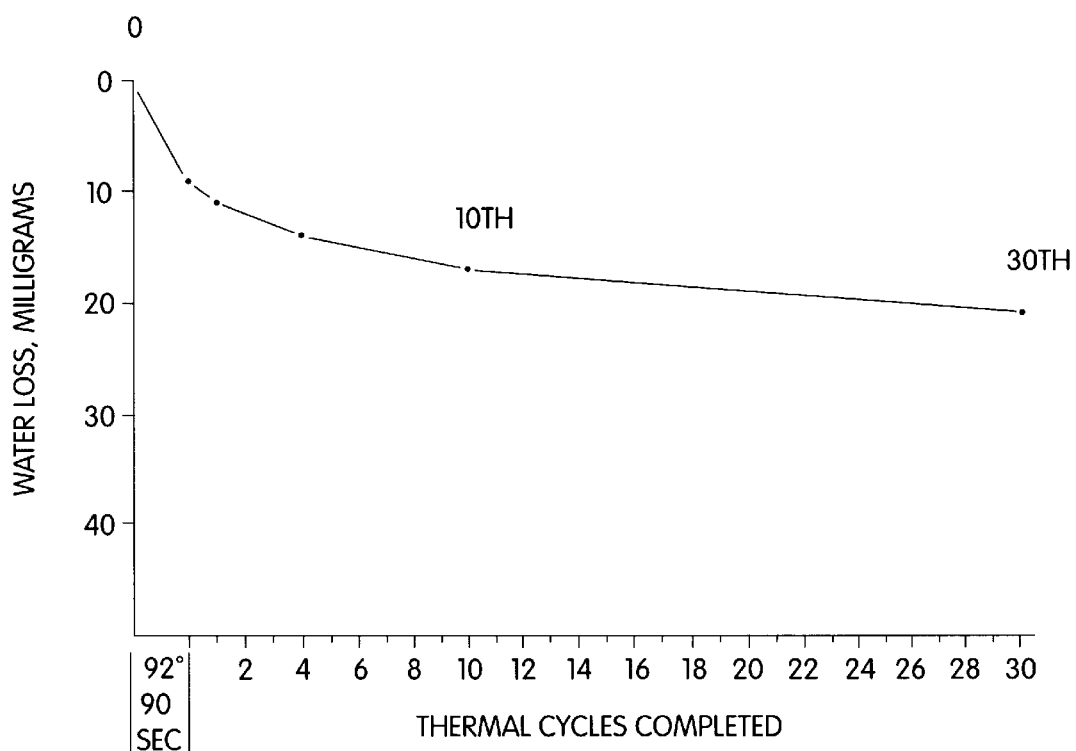
FIG. 4A illustrates the water loss and FIG. 4B the uniformity of a dye solution across a slide during a typical thermal cycling procedure utilizing the method and apparatus of the present invention.
Figure 4B:
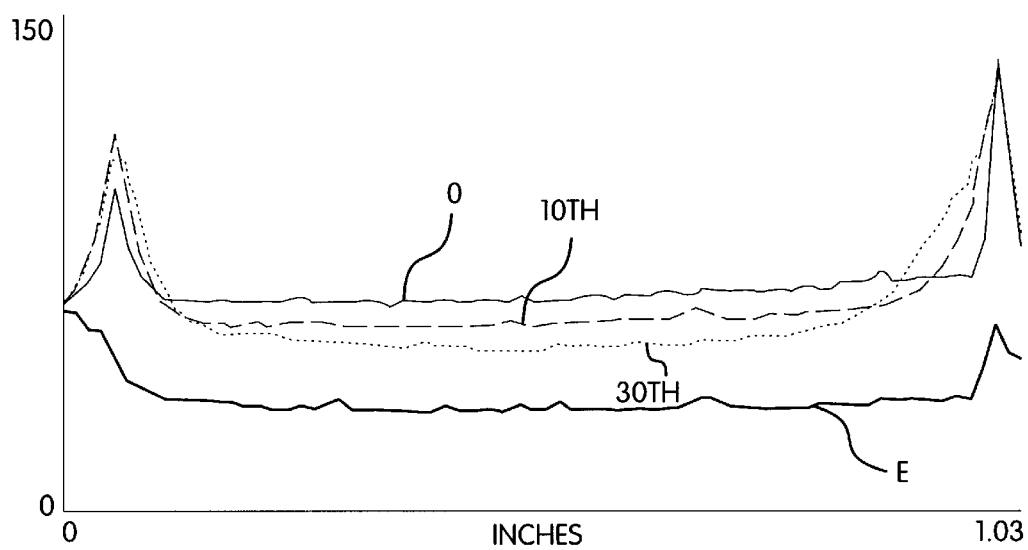

FIG. 4A shows the water loss profile of the slide assembly through the thermal cycling procedure. As expected, it is similar in shape and final water loss to the data from the example illustrated in FIG. 3. The profiles shown in FIG. 4B were taken through the identical section of the slide assembly prior to adding the test solution (E), with the test solution in place but before thermal cycling (0), and after the 10th and 30th thermal cycles. The difference between profiles E and 0 is due to the 50 $\mu l$ of test solution containing the dye. As the slide assembly progresses through the thermal cycling procedure and water evaporates, the cover glass drops (as diagramed in FIGS. 2A–2C). This is reflected by the progressive lowering of the profiles after the 10th and 30th thermal cycles in FIG. 4B. Profiles taken after the 1st and 4th cycles (not shown in FIG. 4B) are, respectively, superimposable on and slightly below the 0 profile. As water evaporates, the dye (and other components) become trapped in the progressively more viscous periphery. This phenomenon is shown by the progressive broadening of the side peaks from 0 through the 10th to the 30th cycle. At the same time, the middle areas the profiles remain essentially flat, indicating uniformity of concentration over the central two thirds of the slides, even after 30 thermal cycles.

Referring now to FIGS. 5A–5D, it will be seen through the examples that the presence of polysucrose of the present invention in an aqueous solution has no adverse effects on the quality or quantity of products made in a standard enzymatic thermal cycling reaction. The reactions were standard polymerase chain reactions well known to the art, designed to produce a single DNA product of about 500 base pairs. The reactions were performed in small closed plastic test tubes (with and without polysucrose) and on a microscope slide, the latter utilizing the present invention as the means to control evaporation. The data are presented as density tracings through lanes of an agarose gel utilized to size separate the reaction products. Density scans were done on a photograph of the ethidium bromide stained gel. Reaction products were loaded at the left and migrated to the right during the electrophoretic separations. The major peak near the center represents the expected product of the reactions. The smaller, broader peak to the right of the major peak represents a primer artifact ("primer dimers") well known to the art.

Figure 5A:
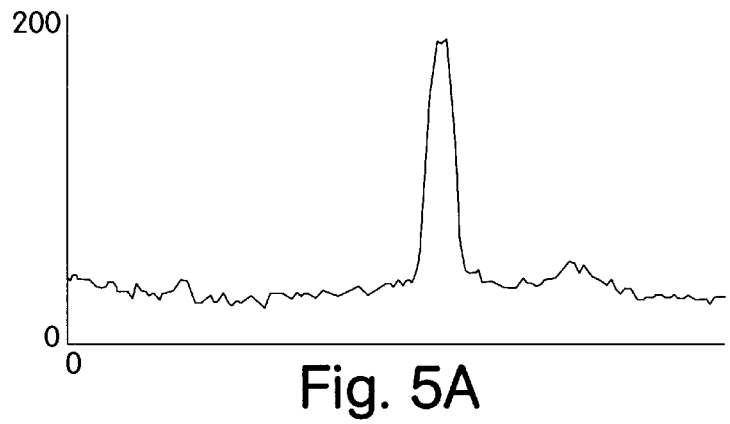
FIGS. 5A–5D illustrate the equivalent results of a standard enzymatic thermal cycling procedure performed in closed test tubes with and without the present invention, and on a microscope slide with the present invention.
Figure 5B:
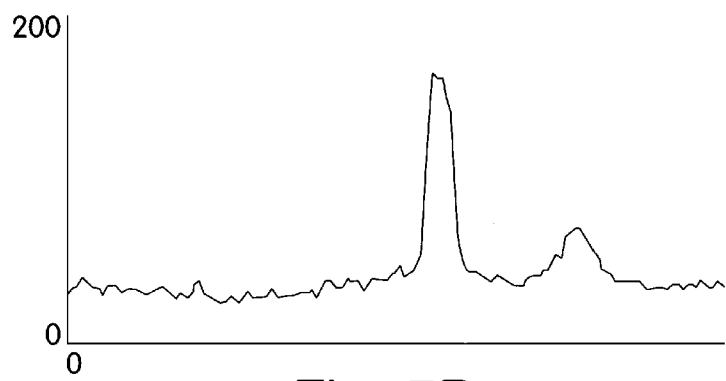
Figure 5C:
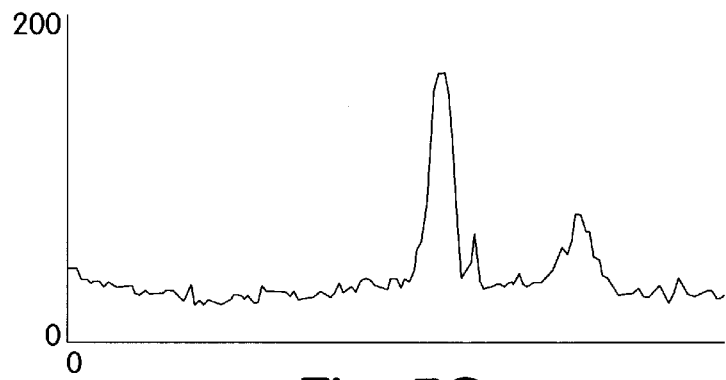
Figure 5D:
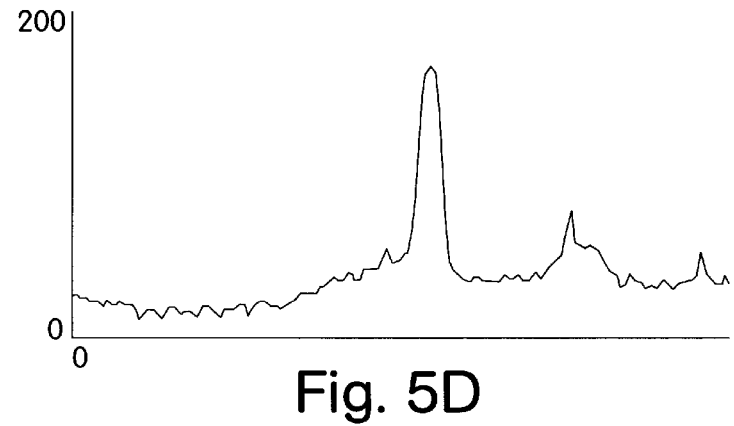

FIG. 5A illustrates the result of a first example in which the standard reaction was performed in a closed tube. FIG. 5B illustrates the results of the same protocol shown in FIG. 5A but for the inclusion of polysucrose, in this case a 10% solution. FIG. 5C is the same protocol as FIG. 5B but for the inclusion of blocking agents required for reactions done on glass vessels. The functional blocking agent included was 0.5% bovine serum albumin, also well known to the art. FIG. 5D is the same protocol as FIG. 5C, except that the reaction was performed on a microscope slide under a cover glass, utilizing the present invention as the sole means to control evaporation. The essential equivalence in the four tracings as to the position and shape of the major band indicates the lack of any adverse effects of the present invention on the quality or quantity of product from a standard enzymatic thermal cycling reaction. In addition, FIG. 5D shows the utility of the present invention even in a minimal volume reaction on a microscope slide. The equivalent solution without the polysucrose evaporates to (or close to) dryness during the thermal cycling reaction, leaving no recoverable liquid to analyze.

Figure 6A:
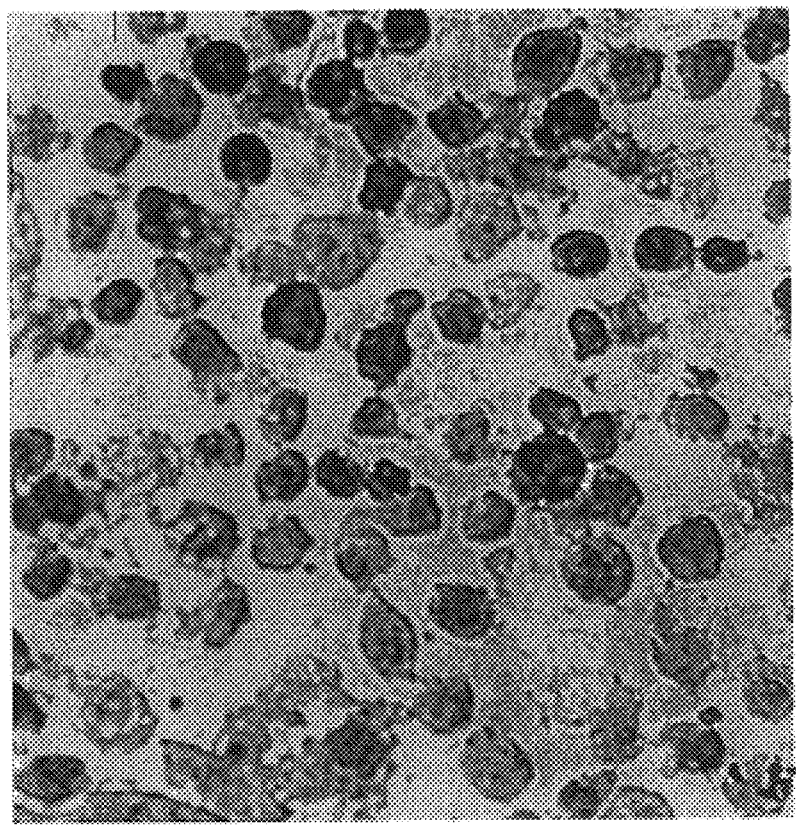
FIGS. 6A and 6B illustrate the detection of specific viral nucleic acids in cells affixed to microscope slides after amplification reactions ("in-situ PCR") done using conventional fingernail polish sealant (FIG. 6A) and using the present invention (FIG. 6B) to control evaporation.
Figure 6B:
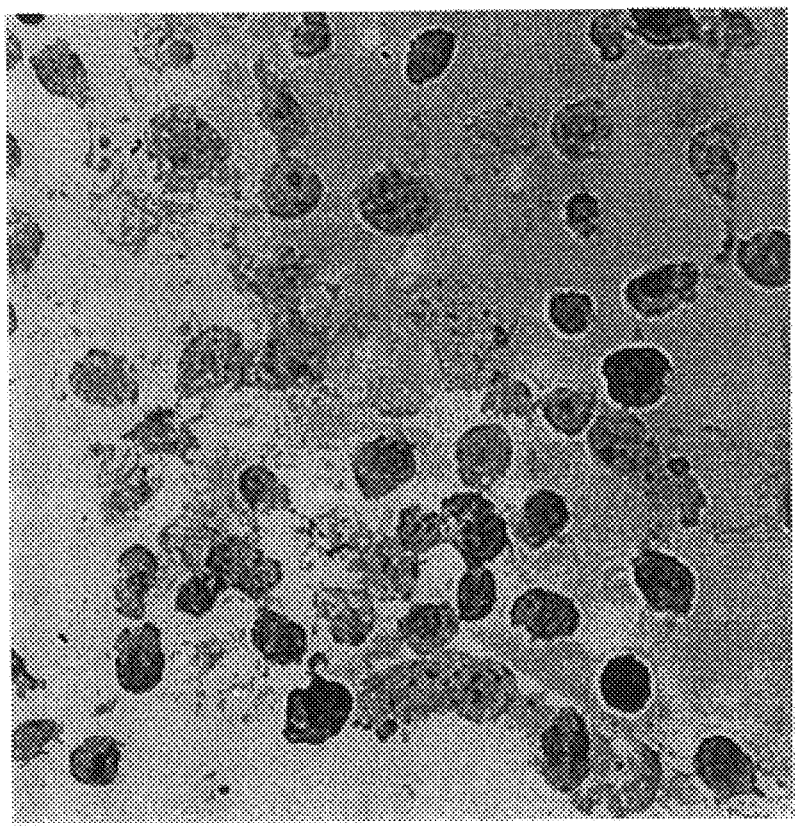

The application of the present invention to thermally cycled nucleic acid amplification reactions performed on tissues affixed to microscope slides is shown in yet another example shown in FIGS. 6A and 6B. Cells infected with HIV-1 ("positives") and uninfected cells ("negatives") were mixed at a ratio of 30% positives and affixed to standard microscope slides. The slides were subjected to the well-known procedure commonly referred to in the art as "in-situ polymerase chain reaction" (In-Situ PCR). The reactions were designed to amplify deoxyribonucleic acid (DNA) sequences specific to the human immunodeficiency virus HIV-1. Positive cells will appear red and negative cells will be gray at the end of the procedure. Except for the polysucrose, the reaction components and protocols were as described in Bagasra, et al., 1995. *Current Protocols in Molecular Biology*, F. M. Ausubel, et al., eds., John Wiley & Sons, Inc., Section 14.8. The enzymatic reaction mixes, one containing 15% polysucrose, were placed on the prepared microscope slides and covered with cover glasses. The slide without the polysucrose was sealed by the traditional method, i.e., fingernail polish. No exogenous sealant was applied to the slide with the polysucrose in the reaction mix. The assembled slides were thermally cycled utilizing a standard protocol without the use of any other means to control evaporation. The thermal protocol was 30 cycles of 94° C., 1 minute; 45° C., 1 minute; and 72° C., 1 minute. After thermal cycling, the slides were processed as per standard protocols, ultimately resulting in the deposition of a dark red dye in the cells where the amplified nucleic acids are located. The slides were analyzed by light microscopy and photos taken of appropriate fields. FIG. 6A is a photograph of the slide processed with the traditional method to control evaporation, i.e., fingernail polish. FIG. 6B is a photograph of the slide which contained the present invention as the sole means to control evaporation during thermal cycling. The two images are equivalent in all important aspects: proportion of dye-positive cells (i.e., HIV-1 positive cells), appearance of the cells (morphology), intensity of staining and lack of non-specific background staining. In summary, the inclusion of the present invention in the in-situ PCR protocol resulted in equivalent data to that from the protocol utilizing the traditional sealing method, fingernail polish.

The procedure used to produce the data shown above in FIG. 6 utilized the present invention for evaporation control in the enzymatic thermal cycling part of the overall protocol. The inventor has found the present invention to be useful in a subsequent step of the protocol, the molecular hybridization step, which is critical for signal specificity. The hybridization procedure typically begins with a heat denaturation step followed by an isothermal incubation, typically from 40–65° C. depending on the components of the hybridization solution. These components can include elevated salts (e.g., over 1 Molar $Na^+$) and/or co-solvents (e.g., 50% formamide). The traditional method of controlling evaporation during hybridization steps is to place the slide assembly in a humidified chamber held at the appropriate temperature. The inclusion of various formulations of the present invention in these hybridization solutions replaces the less convenient forms of evaporation control during the hybridization steps. Therefore, the present invention is useful for in situ hybridizations whether or not used in conjunction with enzymatic steps.

Further Examples and Operation

Microscope slides with affixed tissue are prepared by standard methods to the point where the current invention is to be used. The component(s) of the present invention are included in standard test solutions where evaporation of water must be controlled during the test procedure. After the test procedure utilizing the present invention, the microscope slides are again processed by standard procedures. The following discussion describes a number of applications of the present invention to minimal volume histological procedures.

One example of an application is molecular hybridization wherein a nucleic acid probe molecule (the "probe") is dissolved in the test solution and over time binds specifically to a complementary nucleic sequence (the "target") in the affixed tissues. This procedure is commonly known as "In-Situ Hybridization" or "ISH". The probe molecule specifically bound to the tissue is subsequently detected by a variety of available methods. The present invention can be beneficially used in the hybridization step. A 1× hybridization test solution is prepared containing, for example, 10% to 25% (w/v) polysucrose as well as the standard components of such solutions (salts, probe, buffer, etc.). The solution may also contain co-solvents such as formamide at a typical concentration of 50% (v/v). The test solution is placed on the microscope slide covering the tissue area of interest and a cover glass is positioned on the upper surface of the test solution. The slide is simply placed in an environment at the appropriate temperature and for the appropriate time for the particular experiment. For example, a solution containing 50% formamide and 0.4 Molar sodium salts is typically used at a temperature of 45–50° C., for 2 to 15 hours. There is no requirement for a humidified chamber if the present invention is incorporated into the test solution.

A second class of applications of the present invention is in nucleic acid amplification procedures where an enzymatically catalyzed copying and amplification of a target nucleic acid sequence is performed while the target is affixed to the tissue on the microscope slide. One of these procedures is known as In-Situ Polymerase Chain Reaction ("In-Situ PCR"), a process which applies the Polymerase Chain Reaction (Mullis, U.S. Pat. No. 4,683,202, 1987) to tissues affixed to microscope slides. Another procedure is In-Situ Self-Sustained Sequence Replication-Based Amplification ("In-Situ 3SR"), a process which applies Nucleic Acid Sequence Based Amplification (NASBA) (European Patent No. EP0329822) to tissues affixed to microscope slides. Yet another procedure is primer in situ labeling (PRINS). In all of these procedures and their variants, a small volume of test solution is placed over the tissue on the microscope slide and must be protected from excessive evaporation during the procedure. The In-Situ PCR procedures involve thermally cycling among a variety of temperatures usually including a step over 90° C. The In-Situ 3SR/NASBA procedures are done isothermally at relatively low temperatures (typically 40–50° C.) but require an initial denaturation step of 65° C. or greater. In both the cycling and the iso-thermal amplification methodologies, the use of the present invention would greatly facilitate the procedures by obviating the need for exogenously applied sealants (e.g., fingernail polish) or special equipment and pressure clips to minimize evaporation.

Another class of application of the present invention is in the area broadly defined as immunocytochemistry. Here the test solutions contain an antibody which specifically interacts with a particular type of molecule, if present, in the tissue affixed to the microscope slide. The antibody thereby specifically localized in the tissue is subsequently detected by a variety of methodologies. Immunocytochemistry procedures generally do not utilize temperatures above 37° C. The present invention would be useful in these procedures in the elimination of the need for disposables (e.g., Probe Clips™)and the reduction in slide manipulation by users.

Thus, based on the foregoing description, it can be seen that the present invention provides a number of advantages to minimal volume histological procedures over the current state of the art methodologies used to control evaporation, The present invention is applicable to a wide variety of procedures, not limited in its functional temperature range, easy to use, can be formulated in a variety of ways by the manufacturer and/or by the end user for specific applications, and requires no additional equipment or disposables.

While the above description contains many examples, these should not be construed as limitations on the scope of the invention, but rather as an exemplification of one preferred embodiment thereof. Many other variations are possible. For example, a visible dye can be added to the stock polysucrose solution to more easily allow the user to determine if the material has been used. Also, it may be found that different polymers or combinations of polymers work better for different applications. In addition, the present invention would be generally applicable where aqueous evaporation must be controlled from devices other than standard microscope slides and/or cover glasses. Accordingly, the scope of the invention should be determined not by the embodiments illustrated but by the appended claims.

What is claimed is:

1. A method of conducting a nucleic acid assay on a histological specimen on a microscope slide which comprises positioning a liquid composition between the microscope slide and a cover glass, the liquid comprising an aqueous test solution and 10% to 50% of a dissolved polymeric material selected from the group consisting of polysucrose, polyvinyl pyrrolidone, and polyethylene glycol and wherein the liquid composition is further characterized in that upon being positioned between the microscope slide and the cover glass, the liquid composition defines an interface between the slide and cover glass, whereby upon evaporation of water from the aqueous test solution at the interface, the polymeric material becomes concentrated and reduces further evaporation of water from the aqueous test solution at the interface to thereby enclose a portion of the liquid composition within boundaries defined by the microscope slide, the cover glass and the concentrated polymeric material.

2. The method of claim 1 wherein the polymeric material is an uncharged, water soluble polymer having a molecular weight of at least 1,000.

3. The method of claim 2, wherein the solution and polymeric material inhibit evaporation up to a temperature of about 97° C.

4. The method according to claim 3 wherein the solution and polymeric material inhibit evaporation through a thermal cycling procedure, where the highest temperature in a thermal cycle is at least about 80° C., and a thermal cycling procedure comprises at least 5 thermal cycles.

5. The method according to claim 4, wherein the solution and polymeric material are selected to be suitable for the enzymatic polymerization of nucleic acids.

6. The method according to claim 4 wherein the solution and the polymeric material are selected to be suitable for nucleic acid hybridization.

* * * * *